(12) United States Patent
Viscomi

(10) Patent No.: US 8,002,546 B2
(45) Date of Patent: Aug. 23, 2011

(54) CURE THROUGH LAMINATE VENEER APPLICATOR WITH CURE LIGHT

(76) Inventor: Brian D. Viscomi, Easton, PA (US)

( * ) Notice: Subject to any disclaimer, the term of this patent is extended or adjusted under 35 U.S.C. 154(b) by 297 days.

(21) Appl. No.: 12/315,995

(22) Filed: Dec. 9, 2008

(65) Prior Publication Data

US 2009/0155741 A1 Jun. 18, 2009

Related U.S. Application Data

(60) Provisional application No. 61/007,373, filed on Dec. 12, 2007.

(51) Int. Cl.
*A61C 3/00* (2006.01)
*A61C 3/04* (2006.01)
*A61C 1/14* (2006.01)
*A61C 5/04* (2006.01)

(52) U.S. Cl. ............. 433/141; 433/29; 433/49; 433/226

(58) Field of Classification Search ............. 433/27–31, 433/70, 141–147, 215, 222.1, 140, 226–227, 433/49–50, 3–4; 604/1–3; 132/320, 76.5; 15/244.1; 401/196, 207, 270, 282, 283, 291; 362/602; 601/2–3; 607/88, 89, 92, 93; 385/129, 385/130, 132

See application file for complete search history.

(56) References Cited

U.S. PATENT DOCUMENTS

| | | | |
|---|---|---|---|
| 4,822,278 A * | 4/1989 | Oliva et al. | 433/91 |
| 4,834,654 A | 5/1989 | Naussbaum | |
| 4,953,902 A | 9/1990 | Brown | |
| 4,993,949 A | 2/1991 | Hill | |
| 5,040,981 A * | 8/1991 | Oliva | 433/141 |
| 5,256,064 A * | 10/1993 | Riihimaki et al. | 433/141 |
| 5,759,032 A * | 6/1998 | Bartel | 433/29 |
| 6,102,696 A * | 8/2000 | Osterwalder et al. | 433/29 |
| 6,702,576 B2 * | 3/2004 | Fischer et al. | 433/29 |
| 7,273,369 B2 * | 9/2007 | Rosenblood et al. | 433/29 |
| 2004/0053189 A1 * | 3/2004 | Friedman | 433/29 |
| 2005/0066459 A1 * | 3/2005 | Pinyayev et al. | 15/28 |
| 2005/0270801 A1 * | 12/2005 | Torgerson | 362/615 |
| 2007/0141530 A1 * | 6/2007 | Graham | 433/163 |
| 2008/0014559 A1 * | 1/2008 | Love | 433/226 |
| 2008/0057463 A1 * | 3/2008 | Wong et al. | 433/29 |
| 2008/0166677 A1 * | 7/2008 | Graham | 433/29 |

* cited by examiner

*Primary Examiner* — Todd Manahan
*Assistant Examiner* — Yogesh Patel

(57) ABSTRACT

A veneer applicator to compressively place and photo cure a restorative covering to a tooth to include a photo transmissible insert (2) having a compressible applicator (4) with at least one traversing aperture (6) and a photo transmissible insert shaft (14) to dock with an LED device (22). Docking the insert shaft (14) with the LED device (22) permits a photo curing spectrum to traverse the shaft (14) and compressible applicator (4) at least one aperture (6). This allows for direct surface bonding during veneer application.

9 Claims, 19 Drawing Sheets

CURE THROUGH LAMINATE VENEER APPLICATOR WITH CURE LIGHT

CROSS REFERENCE TO RELATED APPLICATIONS

This application claims the benefit of Provisional Patent Application Ser. No. 61/007,373 filed 2007 Dec. 12, by the present inventor

FEDERALLY SPONSORED RESEARCH

Not Applicable

SEQUENCE LISTING OR PROGRAM

Not Applicable

FIELD OF INVENTION

This invention applies to the field of Dentistry specifically to allow for the simultaneous controlled placement and curing of an indirect dental veneer to a tooth surface with a singular instrument.

BACKGROUND

Prior Art

To enhance the esthetic appearance of a tooth, or restore it to its anatomical original form, it may be necessary to place a tooth-like cover or veneer onto its facial or outer surface. After the tooth is prepared, an impression of it is sent to a laboratory which fabricates the veneer and returns it to the clinician for insertion into the patient's mouth. The intended tooth surface is then prepared to receive the veneer by being etched and primed. Having done this, a bonding agent is applied to the inner surface of the veneer, which is then placed on the tooth and photo-cured to effect the veneer's adhesion to the tooth. The placement process presents with a myriad of challenging steps. This is due to the veneer's innate fragility and size. Typically the clinician will manipulate the veneer for priming and placement with his thumb and index finger. He then places the veneer onto the tooth's surface, positioning as best he can (the veneer has been fabricated to fit precisely on a tooth). Wearing the required latex gloves adds more ergonomic difficulties to an already challenging step. Slippage, mal-placement, and over expression of bonding agents, are just some of the untoward complications which can result from this. Once properly oriented on the tooth, the clinician then exposes the veneer to a curing light to bond it to the tooth. Ideally, it is desirable that upon placement of the veneer, adequate compression be applied as to express excess bonding resin from the periphery of the veneer prior to application of the polymerizing light. The preferred sequence of curing is from the center of the veneer outward. Present placement systems, because of their structural design, present with an opaque central attachment apparatus which prevents the transfer of the light curing medium, with a subsequent lack of cured resin in the critical central portion of the veneer. This area must be addressed after the removal of the placement device. The Cure Through Laminate Veneer Applicator With Cure Light enables the clinician to affix the veneer immovably to an instrument head, accurately position it on the intended tooth surface, and spot cure it in the desired center portion of the veneer without the interruption of changing hand positions or instrumentation. The affixed veneer is in alignment with the instrument's self-incorporated instrument curing light. Thusly, the clinician has both the veneer holding instrument and curing apparatus simultaneously in his hand.

U.S. Pat. No. 4,834,654 to Naussbaum, J. William, May 30, 1989, presents a dental prosthesis applicator which has a generally opaque head covered by an adhesive strip. This opacity does not allow for light transference and hence leaves the critical central portion of the veneer uncured with the initial light application. Furthermore, curing of the veneer is done as a secondary step following veneer placement requiring a change in hand positioning, and an exchange of instruments.

U.S. Pat. No. 4,953,902 to Brown, Martin A., Sep. 4, 1990, presents a veneer placement holder that has an opaque, adhesively covered transfer member which precludes the transfer of a polymerizing light in the center of the veneer during the initial application.

Furthermore this device relies on a sliding plunger to release the veneer when necessary.

The curing of the veneer is then done as a secondary step following veneer placement requiring a change in hand positioning, and an exchange of instruments.

U.S. Pat. No. 4,993,949 to Hill, Sheryl L., Feb. 19, 1991, presents as a thin rod which relies on the application of an adhesive globular mass to envelop the veneer in an irregular, unpredictable fashion for the purpose of transfer and placement of the intended object.

The curing of the veneer is then done as a secondary step following veneer placement requiring a change in hand positioning, and an exchange of instruments.

U.S. Pat. No. 5,040,981 to Oliva, William E., Aug. 20, 1991, presents as a cylindrical tip attached to an extended rod. The tip is festooned with a plurality of flexible tabs meant to engage the veneer for the placement process. These tabs plus their attachment tip are opaque in nature and serve to prevent light transference to the critical central portion of the veneer thus subjecting the veneering process to potential complications by requiring a change in hand positioning, and an exchange of instruments.

U.S. Pat. No. 5,256,064 to Riihimaki, Roy E., Oct. 26, 1993 presents as an applicator with disposable double-sided disposable pads which adhere to the instrument head on one side, and engage the veneer with the other. The instrument head and the double-sided foam pad engage the veneer's central portion, and being opaque in nature serve to prevent light transference to the critical central portion of the veneer opaque by nature and therefore interfere with the transfer of a light source and subject the veneering process to potential complications by requiring a change in hand positioning, and an exchange of instruments.

OBJECTS AND ADVANTAGES

Accordingly, several advantages of the present patent application of Brian D. Viscomi for Cure Through Laminate Veneer Applicator With Cure Light are:
  a. Ergonomically contoured to facilitate approach to tooth
  b. Permits precise placement of veneer on a tooth surface.
  c. Allows for uniform compression of veneer onto tooth surface in order to express excess resin.
  d. Allows for simultaneous light curing while maintaining the applicator in position.
  e. Permits light transference into the critical central portion of the veneer to effect a total resin cure from the center out.
  f. Is disposable.

g. Contains the curing light source within the veneer applicator's handle.

h. Permits one-handed veneer application and curing

It is thus the object of this invention to provide a device to apply and cure dental veneers to a tooth's surface with a singular application and singular instrument.

SUMMARY

In accordance with the present invention, a cure through veneer applicator with a cure light comprises an instrument to compressively place and bond a laminate veneer to the surface of a tooth and simultaneously cure the laminate, possessing a gripping body with thereon a compressible body with at least one traversing aperture to permit the passage of a photo curing light during the operative bonding of a laminate veneer to a tooth surface, and an accompanying light source to provide the curing means.

DRAWINGS FIGURES

In the drawings, closely related figures have the same number but different alphabetic suffixes.

DRAWINGS

Numbers

Figure 1A:
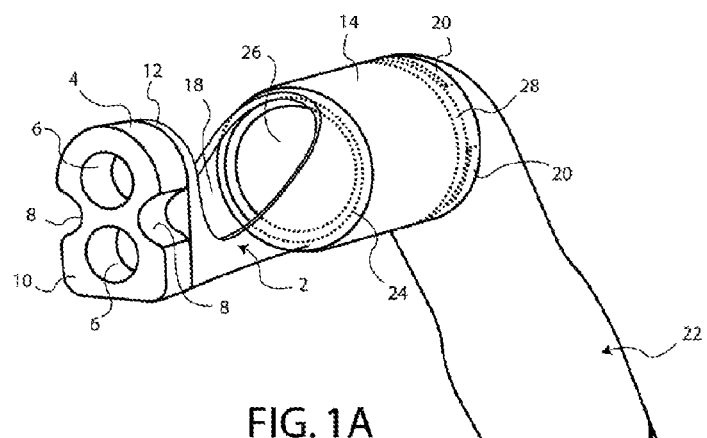
FIGS. 1A to 1B show a frontal three quarter view and lateral orthographical view of a cure through laminate veneer applicator with LED light.

2. Cure through compressible insert
4. Compressible applicator
6. Compressive curing aperture
8. Light channel
10. Adhesive surface
12. Applicator head
14. Insert shaft
16. docking aperture
18. Viewing aperture
20. Snapping protrusion
22. LED device
24. Insert docking shaft
26. LED lamp
28. Circumferential snapping ring
30. LED Power switch
32. Detachable power source
34. Charging surface
36. Emulsion cover aperture
38. Operator
40. Laminate veneer
42. Tooth surface
44. Compressive forces
46. Photo curing light
48. Fiber optic shaft
50. Internal power source
52. Shaft aperture
54. Transparent compressible applicator
56. Contoured surface applicator
58. Transparent applicator holder
60. Compressible applicator
62. Opaque applicator holder
64. Flexible aperture extension
66. Gripping ring
68. Tubular foam applicator sleeve
70. Expandable sleeve insert

DETAILED DESCRIPTION

FIGS. 1A to 3B—Preferred Embodiment

Figure 1B:
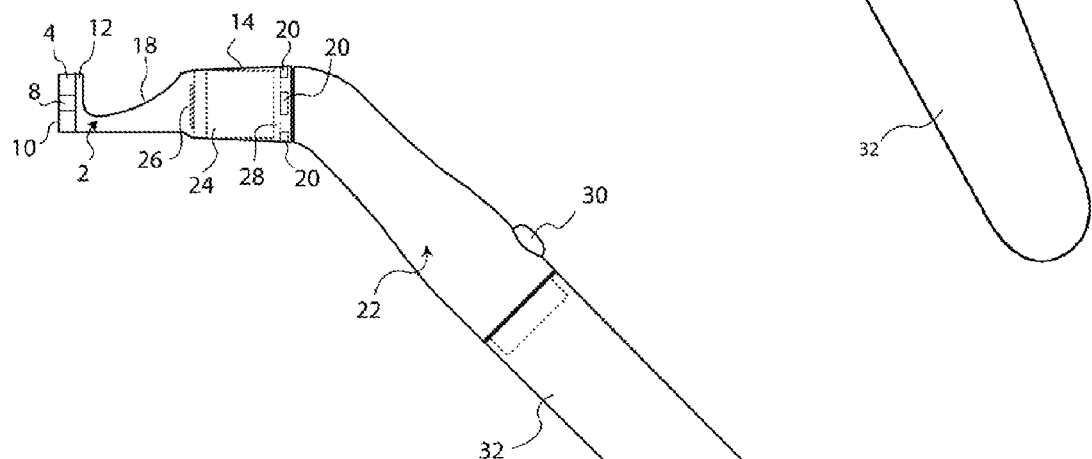
Figure 2A:
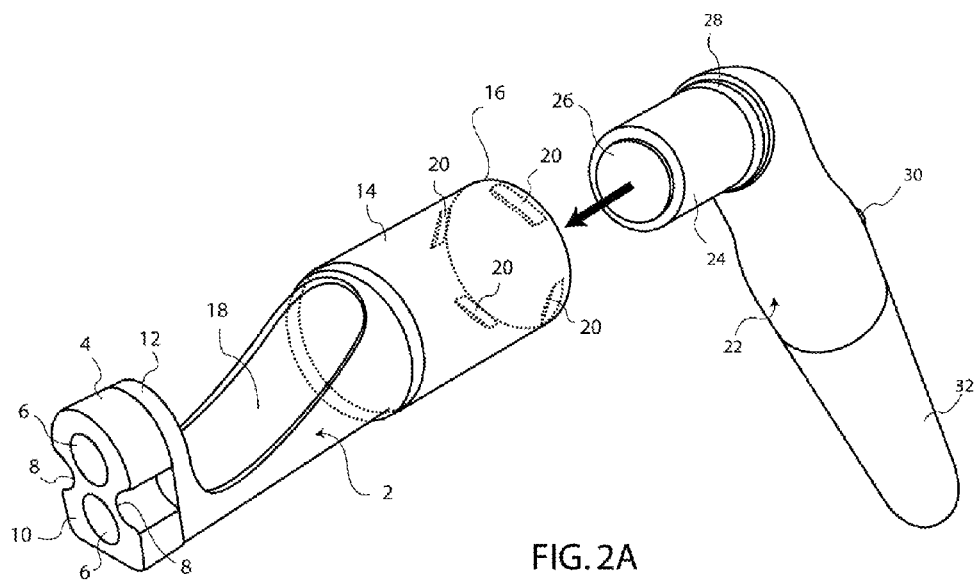
FIGS. 2A to 2B show anterior and posterior dimensional views of a cure through compressible insert undocked from the led light's docking shaft.
Figure 2B:
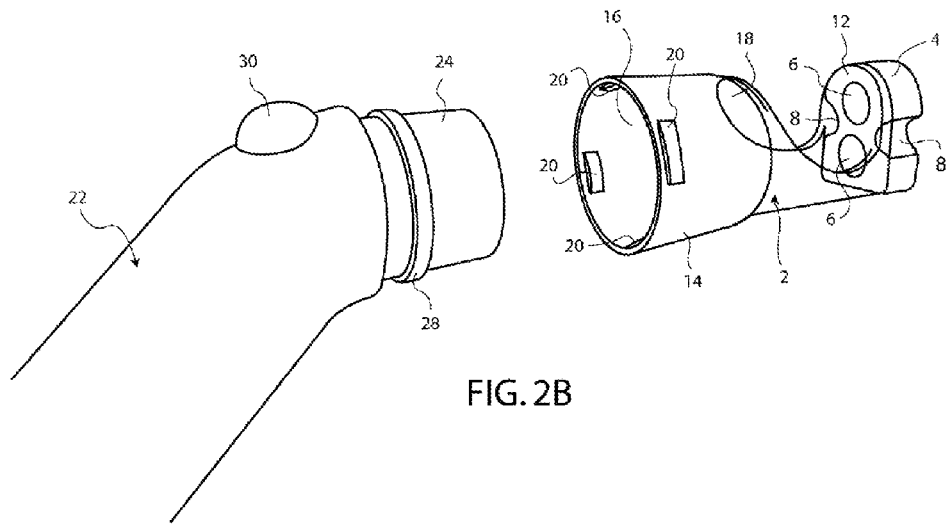
Figure 3A:
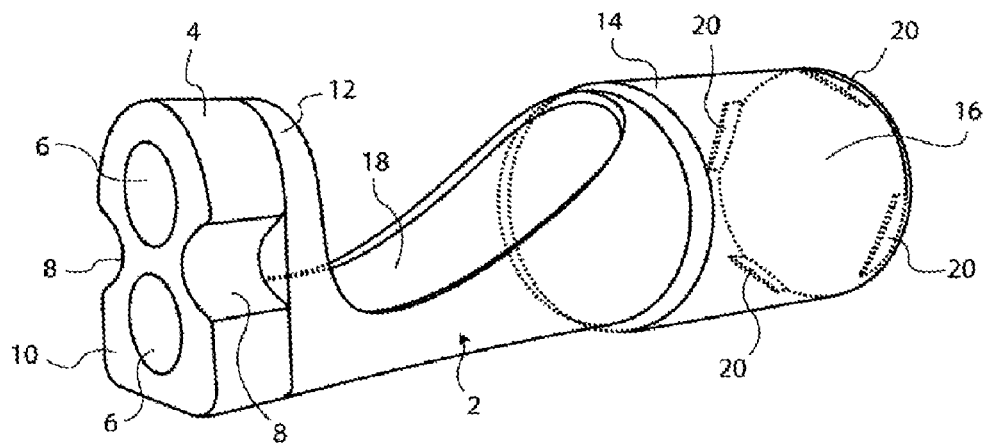
FIGS. 3A to 3B show anterior and posterior dimensional views of the cure through compressible insert having a viewing aperture, insert shaft, and snapping protrusions.
Figure 3B:
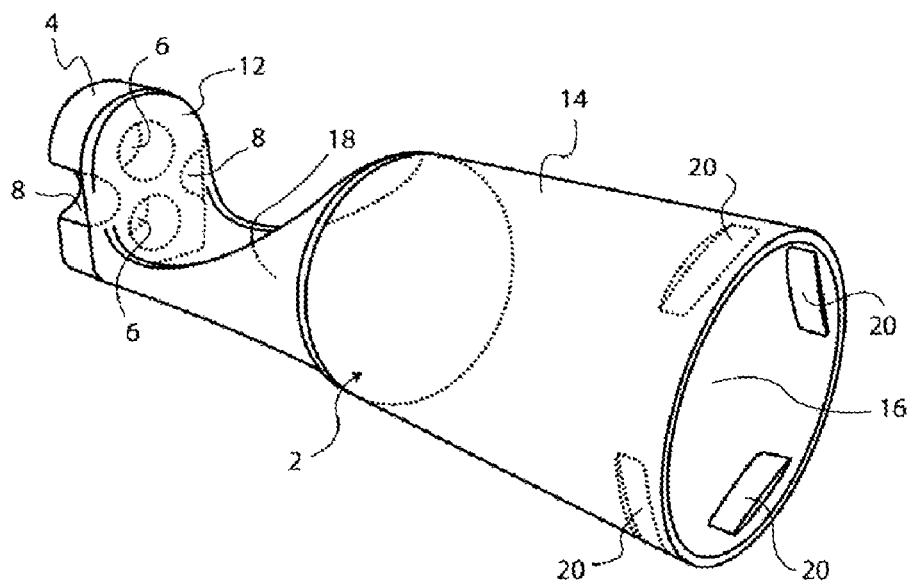
Figure 4A:
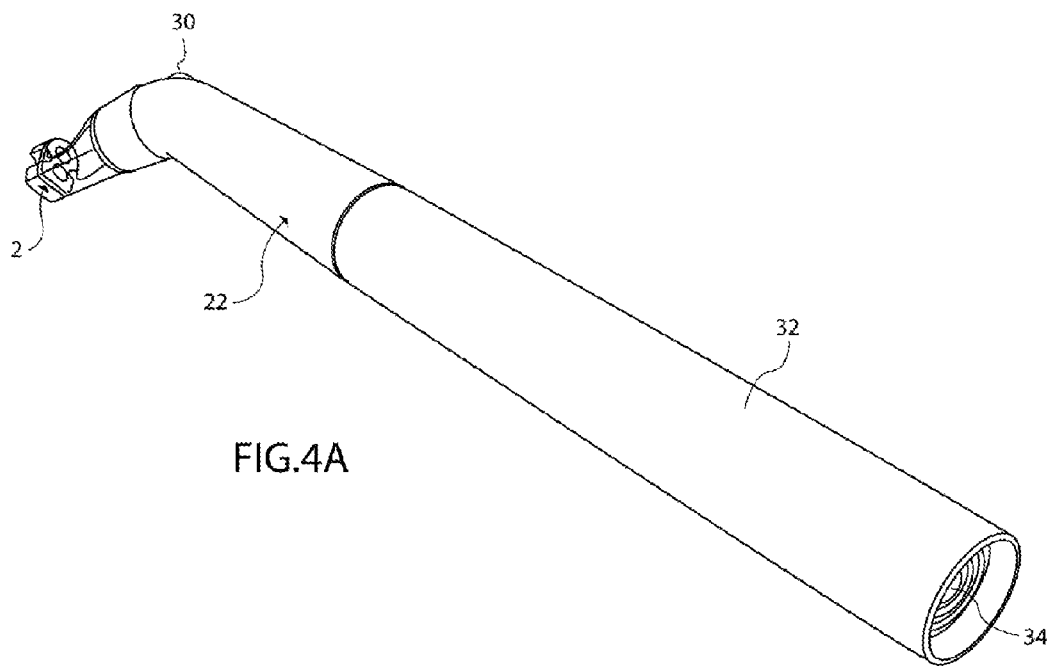
FIGS. 4A to 4B show views of a battery re-charging surface.
Figure 4B:
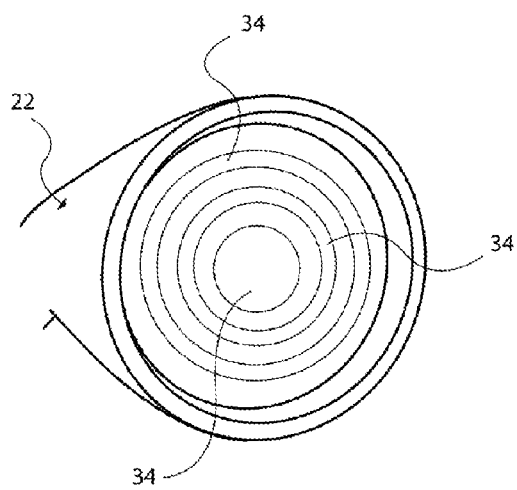

A preferred embodiment of the cure through veneer applicator with LED light is illustrated in FIG. 1A (anterior three quarter view), FIG. 1B (lateral orthographic view), FIG. 2A Anterior undocked dimensional view), FIG. 2B (Posterior undocked dimensional view), FIG. 3A (anterior dimensional view of the applicator portion) and FIG. 3B (posterior dimensional view of the applicator portion). The cure through veneer applicator has two primary aspects. The first is a disposable photo transmissible attachment or cure through compressible insert 2. This insert 2 is designed to interlock and attach with a slender handheld photo curing LED device 22. The LED device 22 is based upon currently available technologies. The attached combination of cure through insert 2 and LED device 22 desirably correlates both portions. This combined correlation permits the transmission of curing LED light from the LED device 22 through the cure through compressible insert 2 and onto to a desired surface.

The cure through compressible insert 2 is a hollowed tubular one piece plastic body with a soft pliant termination or compressible applicator 4. The applicator 4 is comprised of desirably soft closed cell foam or similarly elastic photo transmissible rubberized material such as silicone. The compressible applicator 4 shape is intended to correlate with the general dimensions of a tooth's anterior surface. Thus, the superior portion of the applicator 4 has a curved, semicircular dimension to correlate with a tooth's natural gingival contour. The lateral applicator 4 aspects are optimally shaped to correlate with a tooth's buccal lingual contours while the inferior applicator 4 portion relates to incisal tooth anatomy. Additionally, the compressible applicator 4 contains two openings, holes or curing apertures 6. These apertures 6 are integrally formed within the periphery and traverse the compressible applicators 4 body. They are desirably sized and positioned to primarily transmit photo curing light from the LED device 22 to a bonding surface. Secondarily the curing apertures 6 serve to enhance adaptive compressibility by reducing applicator 4 bulk. Formed into the applicators 4 periphery are two semicircular insets, grooves or light channels 8. The channels 8 are desirably inset to enhance photo curing exposure and compressibility while maintaining applicator 4 surface area. To facilitate veneer placement, an adhesive application 10 for gripping veneers is applied to the compressible applicators 4 operative surface.

The compressible applicator 4 is attached to a flat plastic base, platform or applicator head 12. The applicator head 12 is the terminal portion of a compressible insert's 2 hollow plastic body. It has a flat planar surface and serves as a point of adhesive attachment for the compressible applicator 4. To ensure correlative union, the applicator head 12 shares a relative peripheral dimension with the compressible applicator 4. Extending continuously from the applicator head 12 is the cure through inserts 2 elongated tubular portion. This hollow structure or insert shaft 14 has a mildly flaring dimension as it extends towards an opened termination. This opened second termination or insert docking aperture 16 functions to interface with the LED device 22 in a manner that will align the compressible applicator 4 and curing apertures 6 with a LED lamp 26 curing light emission.

The insert shaft 14 also has a secondary and conspicuously exposed opening or viewing aperture 18 that extends from the posterior surface of the applicator head 12 to a desirable distance within the insert shaft 14. It is desirably sized and open to permit an enhanced clinical observance during operative procedures. Lastly, extruding from the interior circumference of the insert shaft's 14 docking aperture 16 are four raised bumps, humps or snapping protrusions 20. These protrusions 20 are formed on the internal circumferential of the insert shaft 14, just shy of the docking aperture 16 termination. They are designed to interlock with the LED devices 22 insert docking shaft 24.

The Insert docking shaft 24 is a cylindrical and desirably long extension designed to fit within the compressible cure through applicators 2 hollow insert shaft 14. Insertion is accomplished by inserting the docking shaft 24 into the docking aperture 16. Internally housed within the insert docking shaft 24 is a photo light source or LED lamp 26. The lamp 26 is one that is commonly found in commercially available dental devices and emits light from the insert docking shafts 24 termination. Extruding from the docking shafts 24 posterior area is a circumferential extruded band or snapping ring 28. This raised circumferential ring 28 shares an interlocking relationship with the cure through compressible inserts 2 snapping protrusions 20. When a cure through insert 2 is fully inserted into the LED devices 22 insert docking shaft 24, the snapping protrusions 20 engage the circumferential snapping ring 28 to securely fasten for operative procedures. This is similar to a snap on marker cap.

The led lamp 26 is activated by a finger operated LED power switch 30 and is ergonomically positioned to permit optimal finger depression during an operative procedure. To provide the necessary power, an external power source 32 is used. Located on the inferior portion of the external power source 32 are a series of charging surfaces 34 designed to interface with an external charger.

The cure through compressible insert 2 and compressible applicator 4 may be made by injection molding. The applicator 4 can also be fabricated as a separate portion by die stamping. The LED device 22 can be created by modifying existing light devices to permit an interlocking attachment with the cure through compressible applicator 2

FIGS. 12-33 Alternative Embodiments

Figure 11A:
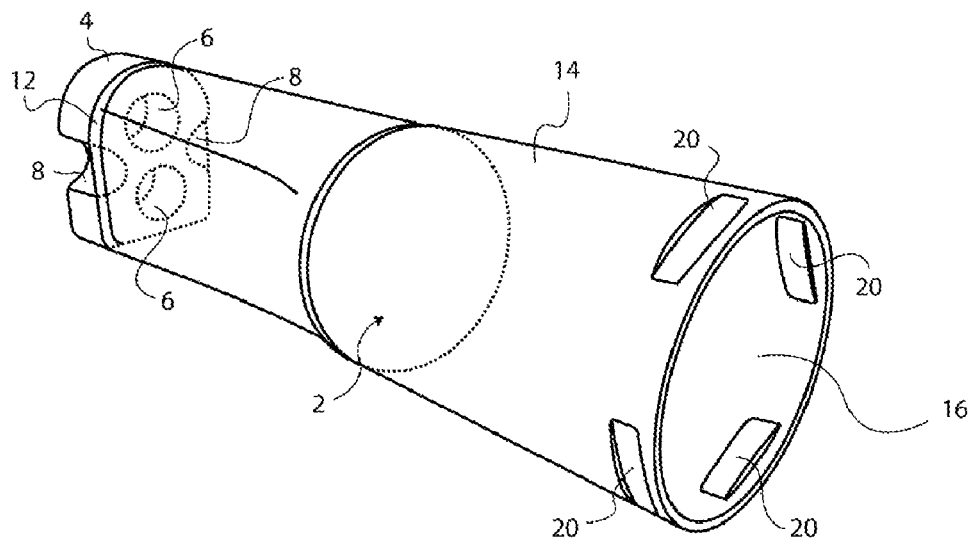
FIGS. 11A to 11B show anterior and posterior views of a cure through compressible insert having no viewing aperture.
Figure 11B:
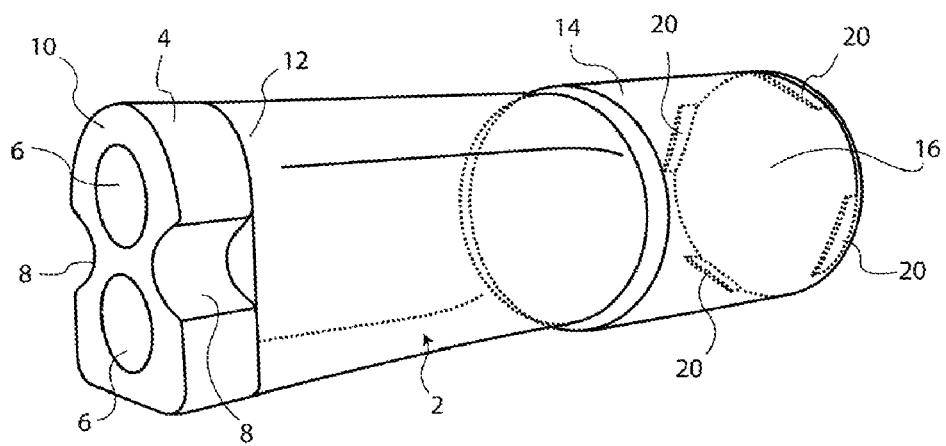
Figure 12:
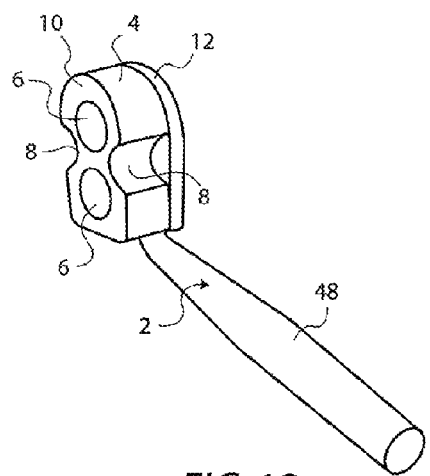
FIG. 12 shows a cure through veneer applicator having a cure through compressible insert with a photo transmitting fiber optic shaft and a LED device having a shaft aperture.
Figure 13:
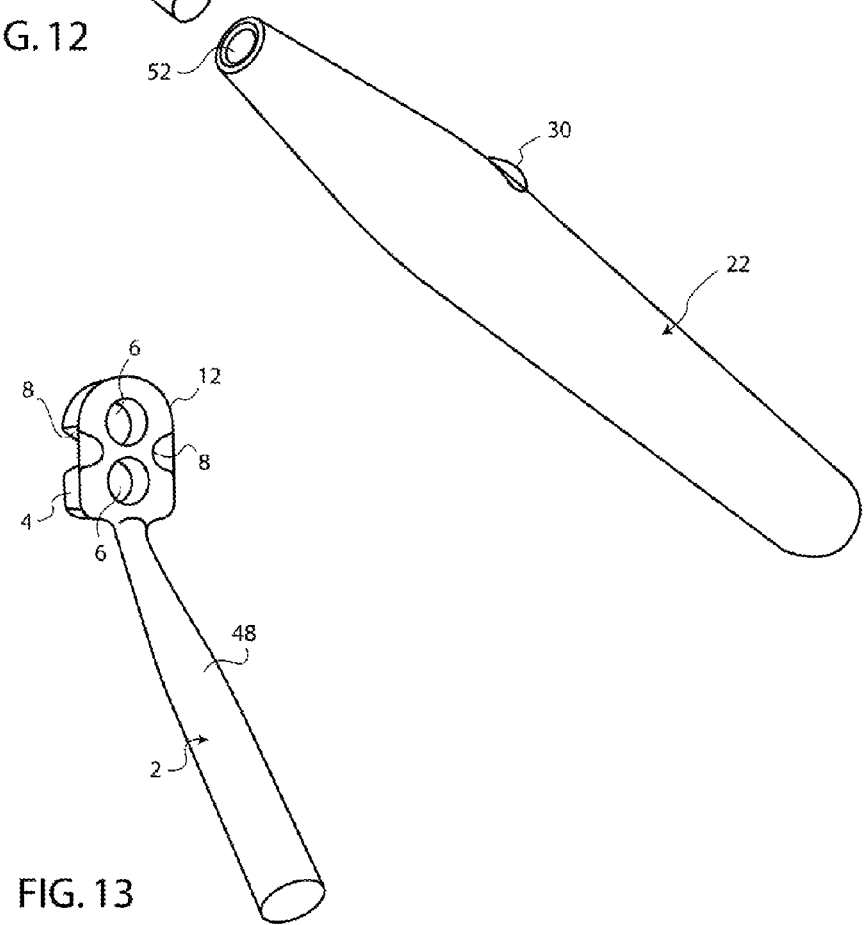
FIG. 13 shows a posterior dimensional view of a cure through compressible inset with a photo transmitting fiber optic shaft.
Figures 14A, 14B:
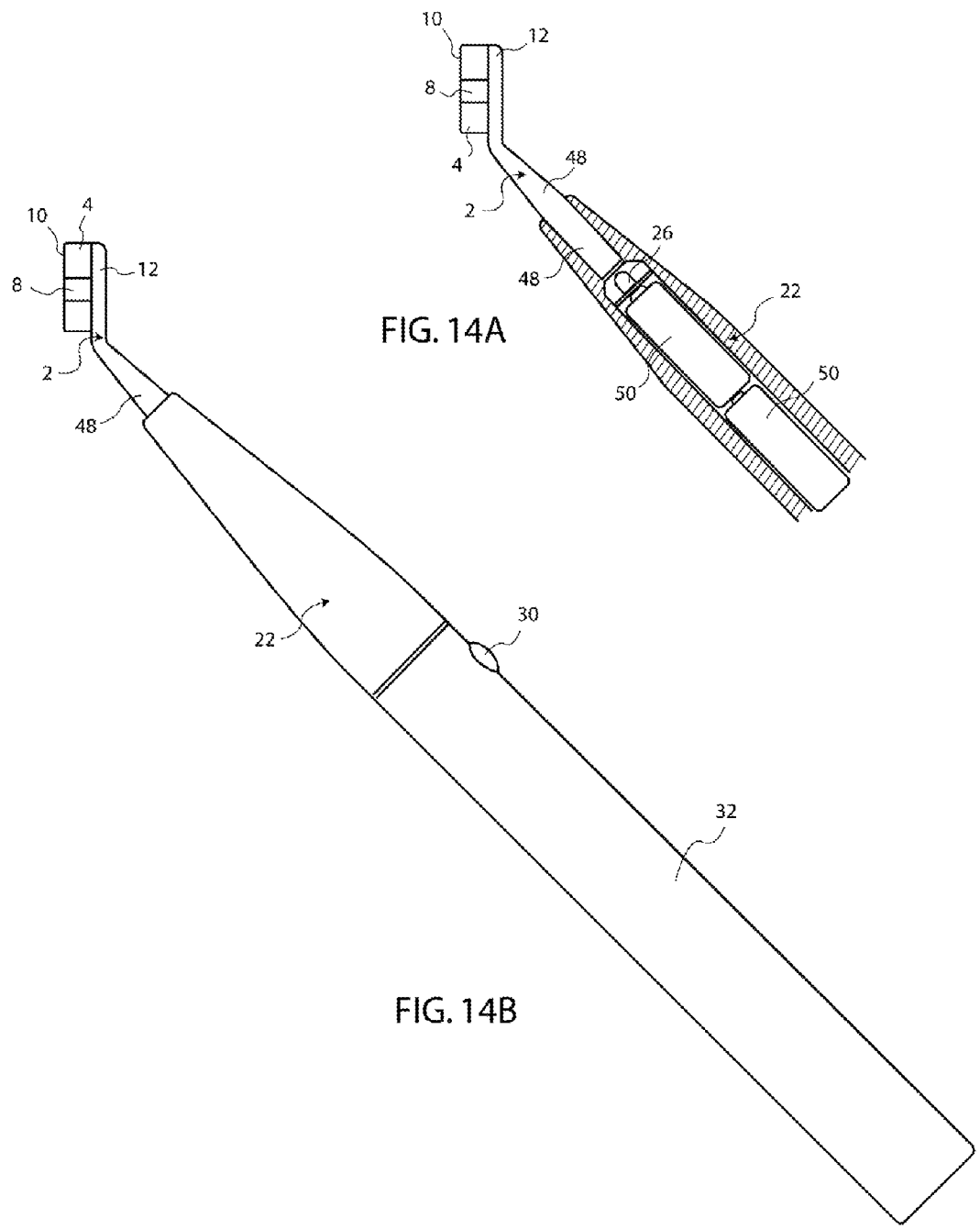
FIGS. 14A to 14B show lateral internal and external orthographic views of a cure through veneer applicator having a cure through compressible insert with a fiber optic shaft.
Figure 15:
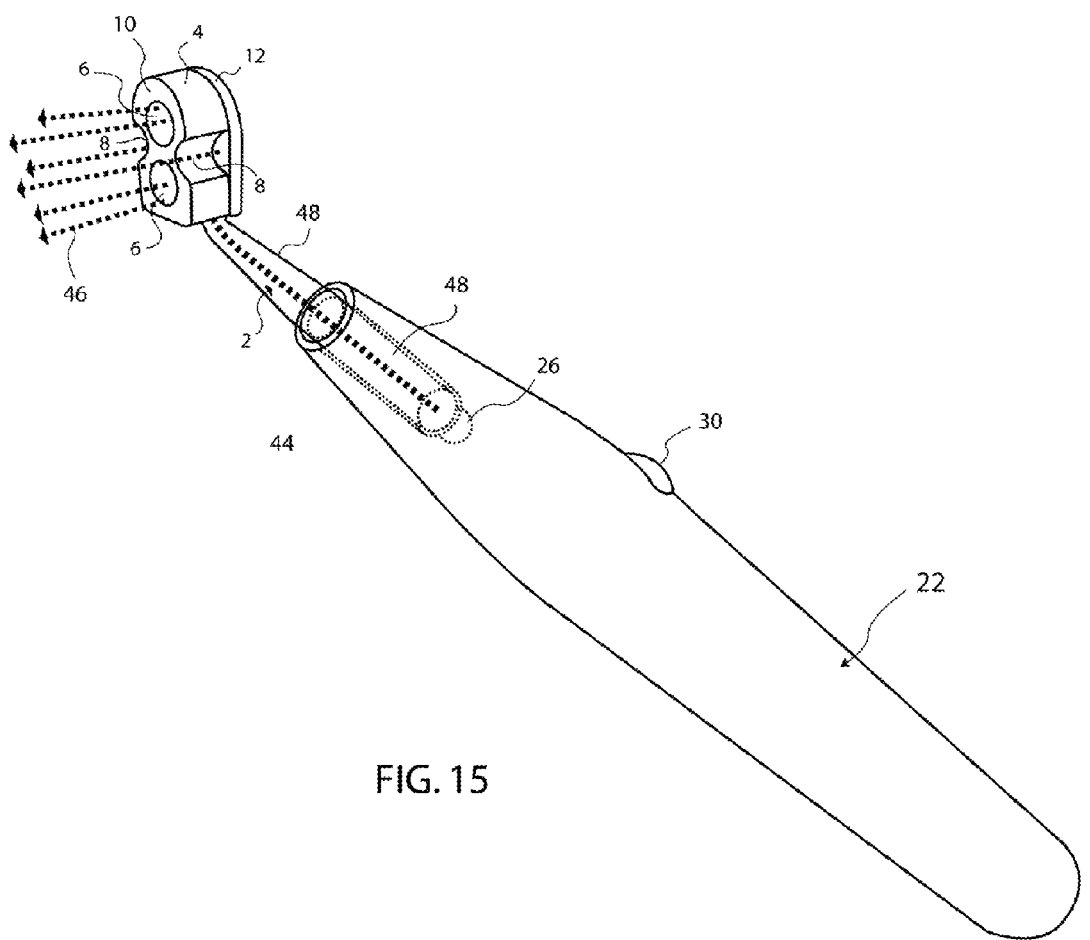
FIG. 15 Shows a LED lamp transmitting photo curing light through the fiber optic shaft to the compressible curing apertures.
Figure 16:
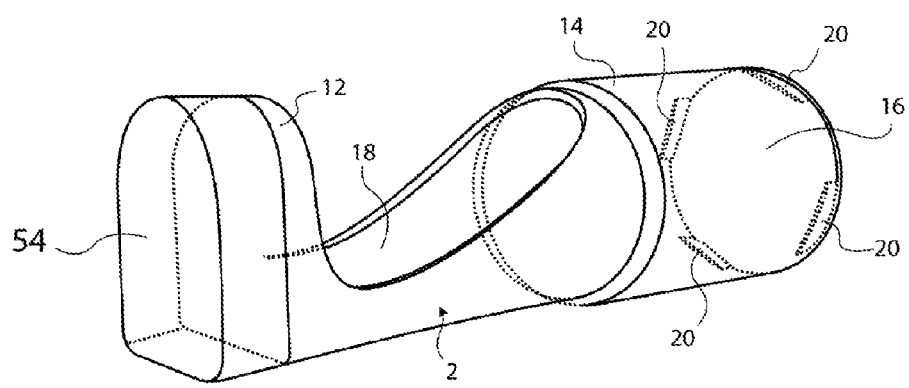
FIG. 16 shows a cure through compressible insert having a transparent compressible applicator made from a suitable compressible silicone material.
Figure 17:
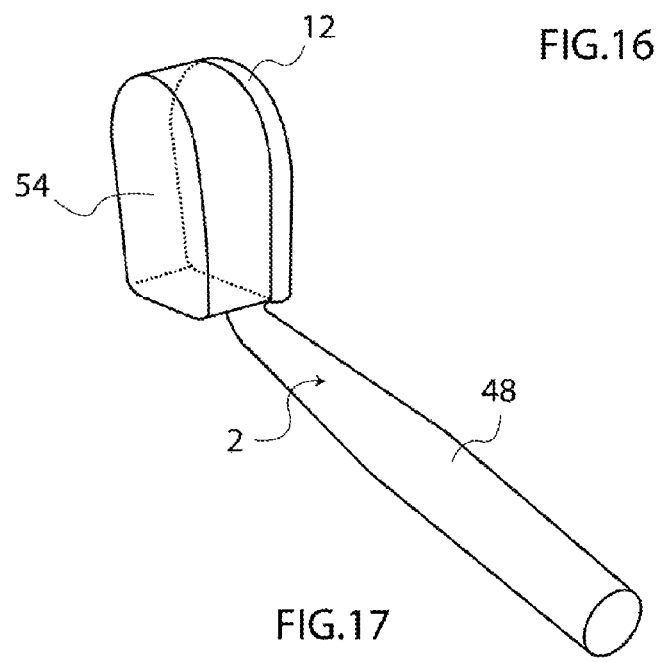
FIG. 17 shows a cure through compressible insert with a fiber optic shaft having a transparent compressible applicator made from a suitable compressible silicone material.
Figure 18:
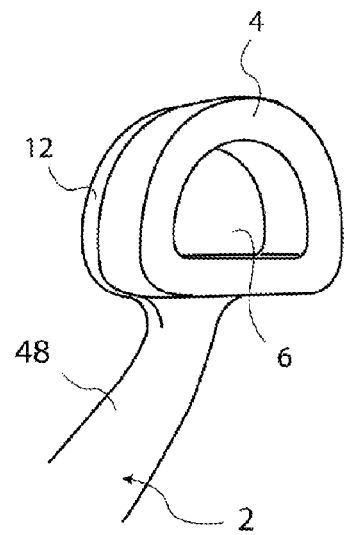
FIG. 18 shows a cure through compressible insert with a fiber optic shaft having a compressible applicator with a single curing aperture.
Figure 19:
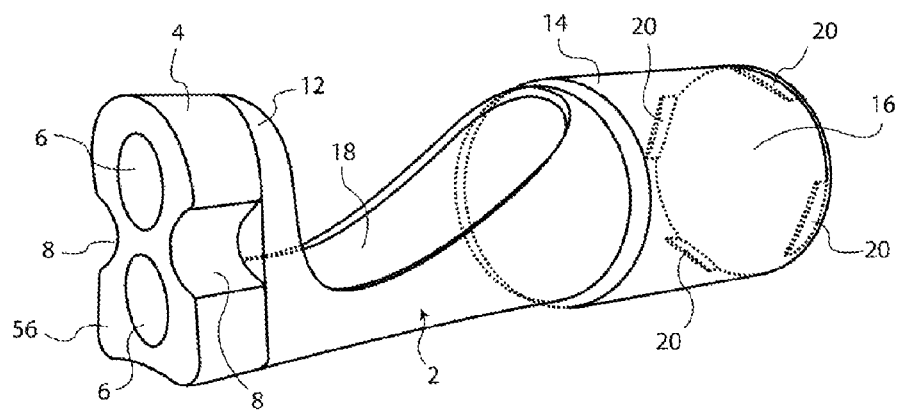
FIG. 19 shows a cure through compressible insert with a concave contoured surface applicator that correlates with a tooth's natural convexity.
Figure 20:
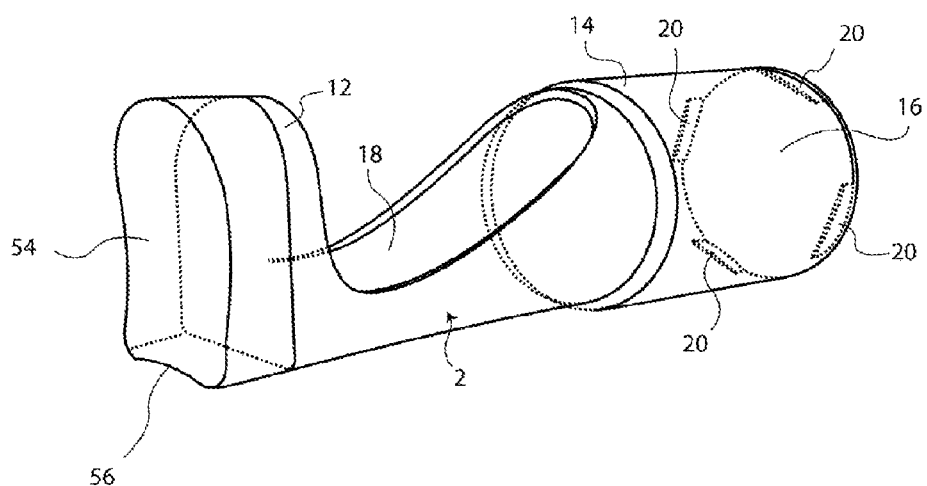
FIG. 20 shows a cure through compressible insert with a concave contoured transparent surface applicator and no curing apertures.
Figure 21:
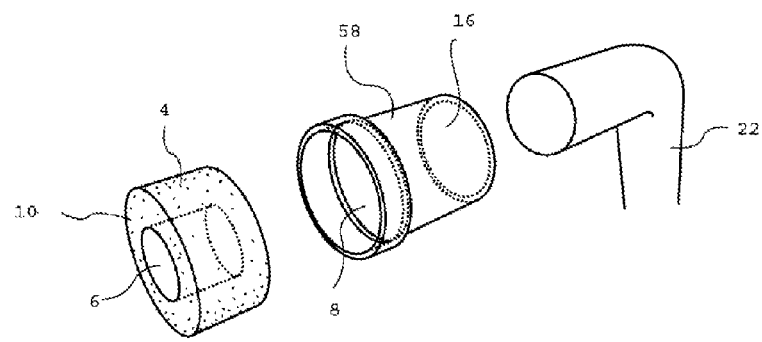
FIG. 21 shows a compressible applicator with a cure through applicator attached to a transparent tubular applicator holder.
Figure 22:
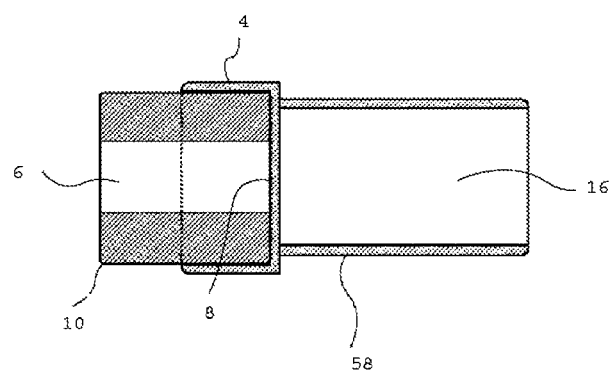
FIG. 22 shows a cross section of the applicator of FIG. 21 to reveal the continuity of the applicator's aperture.
Figure 23:
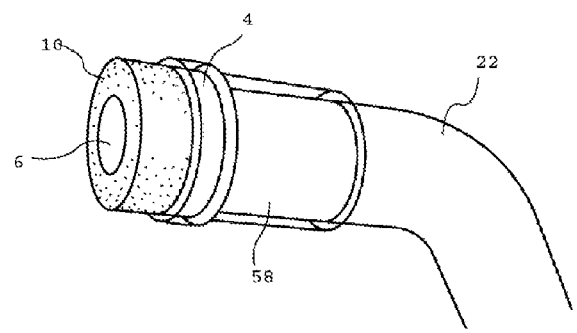
FIG. 23 shows the applicator of FIG. 21 affixed to a light shaft.

There are various possibilities with regard to the configuration of the cure through compressible insert and also the method of photo transmission. FIGS. 11A to 11B show a cure through compressible 2 insert with no viewing aperture 18. FIGS. 12 through 15 show a compressible cure through insert 2 having a fiber optic shaft 48. The shaft 48 is designed to dock with the LED devices 22 docking shaft apertures 52. Upon docking, an internally located LED lamp 26 transmits photo curing light 46 through the fiber optic shaft 48 to the compressible applicators 4 curing apertures 6. The LED light device uses an internal power source 50. FIG. 16 shows a cure through compressible insert 2 having a transparent compressible applicator 54 made from a suitable compressible silicone material. FIG. 17 shows a cure through compressible insert 2 with a fiber optic shaft 48 having a transparent compressible applicator 54 made from a suitable compressible silicone material. FIG. 18 shows a cure through compressible applicator 2 with a contoured surface applicator 56 that correlates with a tooth's natural convexity. FIGS. 19-20 show a tubular, transparent cure through applicator holder 58 with an insertion aperture 16 to frictionally engage an LED device 22 on one end, and compressible applicator 54 with a cure through aperture 6 having an adhesive surface 10 on the opposite end. FIGS. 21-23 show a tubular, transparent cure through applicator holder 62 with an insertion aperture 16 to frictionally engage LED device 22 on one end, a compressible applicator 4 with a cure through aperture 6 having an adhesive surface 10 and a solid transparent light channel 8.

Figure 24:
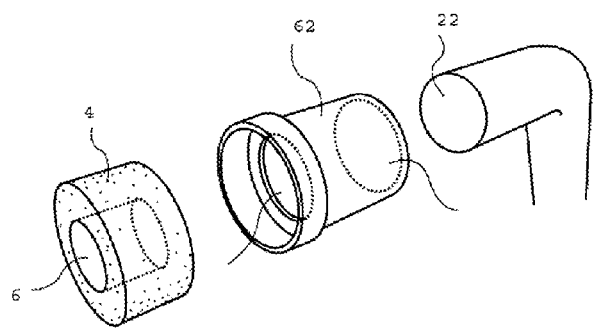
FIG. 24 shows a compressible applicator with a cure through applicator attached to an opaque tubular applicator holder.
Figure 25:
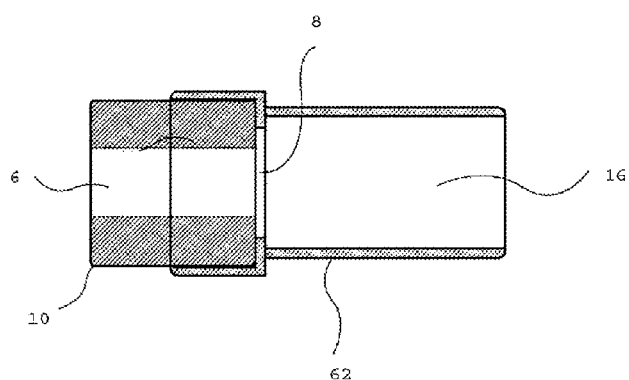
FIG. 25 shows a cross section of the applicator of FIG. 24 to reveal the continuity of the applicator's aperture.
Figure 26:
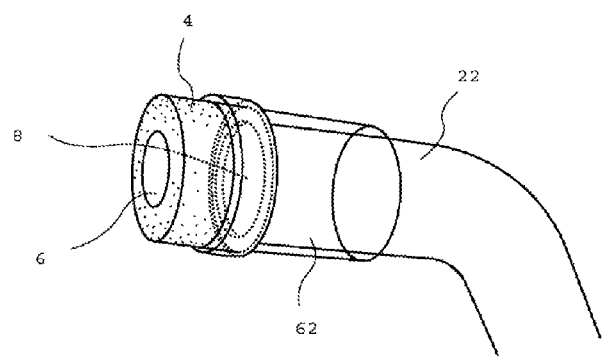
FIG. 26 shows the applicator of FIG. 24 affixed to a light shaft.
Figure 27:
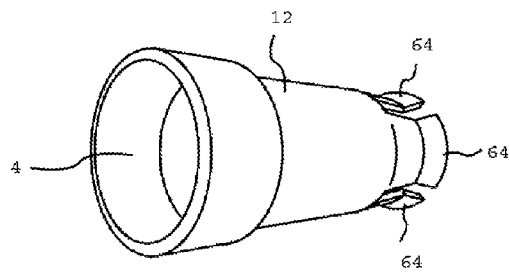
FIG. 27 shows an applicator holder with flexible extensions to adjust and conform while attaching to the light shaft.
Figure 28:
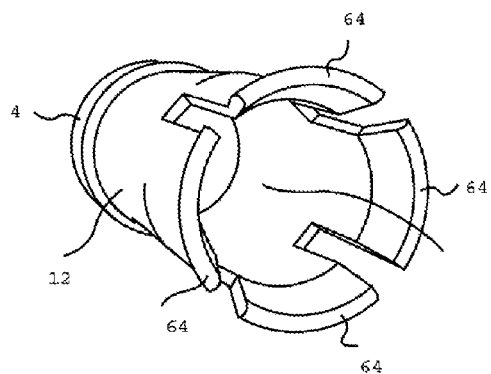
FIG. 28 depicts the a close up of the adjustable extensions.
Figure 29:
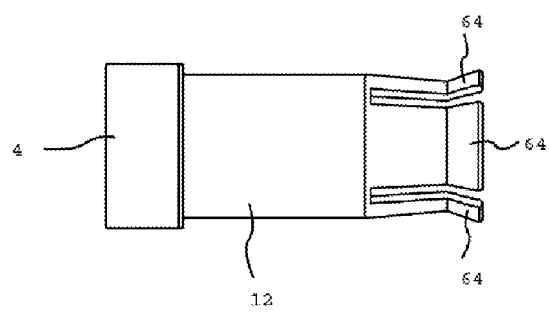
FIG. 29 shows a cross section of the applicator holder of FIG. 27.
Figure 30:
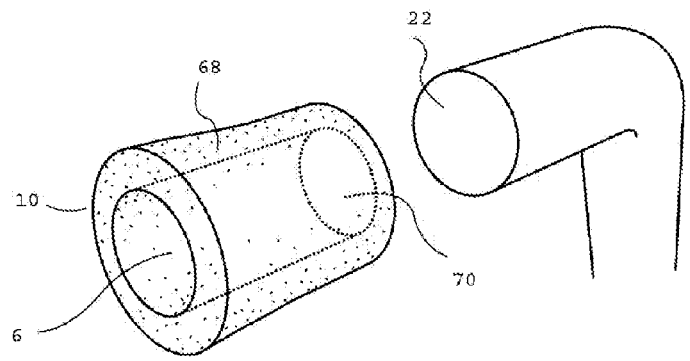
FIG. 30 shows an applicator holder in the form of a compressible foam sleeve whose insertion aperture compressively adapts to the light shaft.
Figure 31:
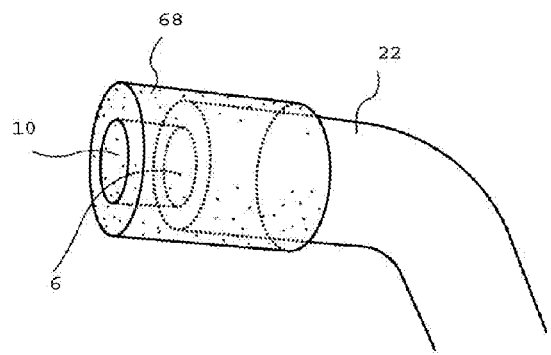
FIG. 31 depicts the sleeve of FIG. 30 attached to the light shaft.
Figure 32:
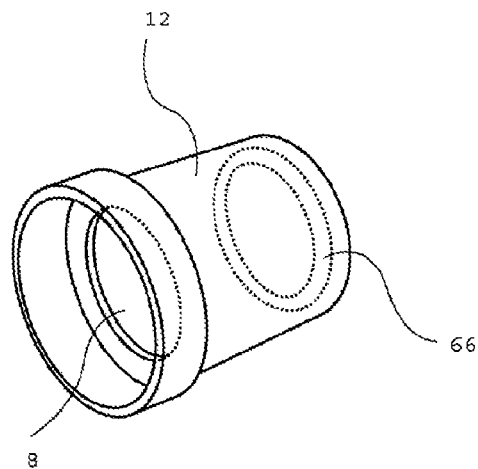
FIG. 32 shows a tubular opaque applicator holder which possesses a compressible gripping ring which engages and secures the holder to the light shaft.
Figure 33:
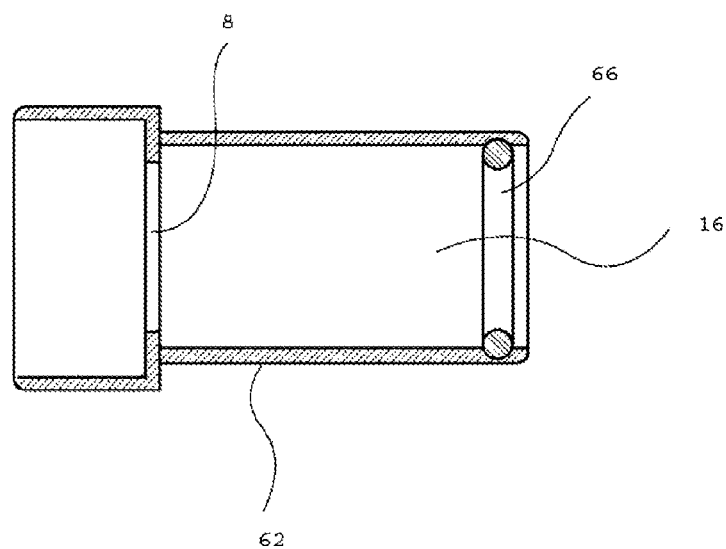
FIG. 33 shows a cross section of the applicator of FIG. 32.

FIGS. 24-26 show a tubular, opaque cure through applicator holder 62 with an insertion aperture 16 to frictionally engage an LED device 22 on one end, a compressible applicator 4 with a cure through aperture 6 having an adhesive surface 10 and a light channel 8 having an aperture. FIGS. 27-29 show a tubular opaque 62, cure through applicator holder with an insertion aperture 16 to frictionally engage an LED device 22 by means of flexible aperture extensions 64. FIGS. 30-31 show a foam tubular cure through applicator sleeve 68 with an expandable sleeve insertion aperture 70 to allow for the insertion of a LED device 22 and, a cure through aperture 6 with an adhesive surface 10 on the opposite end. FIGS. 32-33 show an opaque cure through applicator holder 62 with a circumferential, expandable gripping ring 66 to frictionally engage and retain an LED device 22.

Operation

Figure 5A:
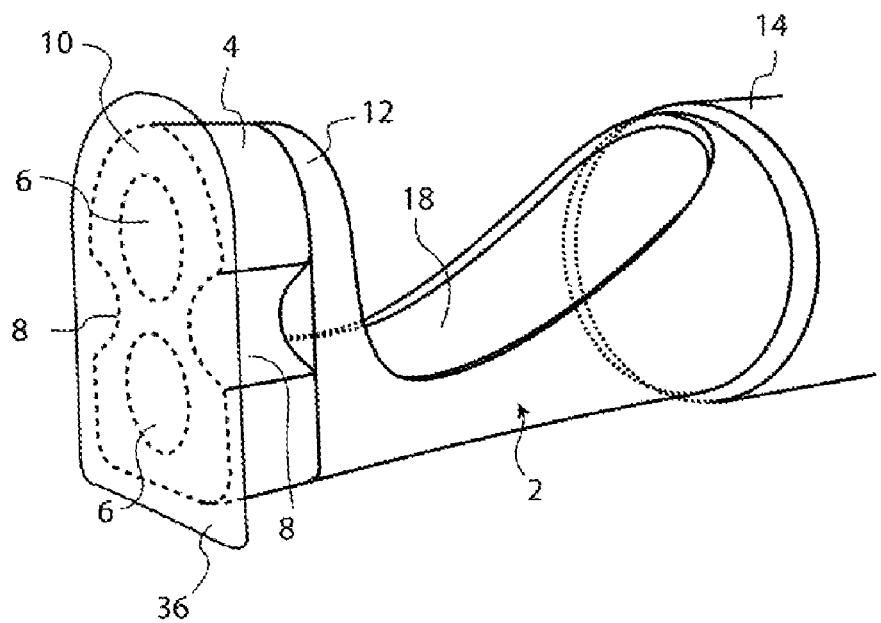
FIGS. 5A to 5B show details of an emulsion cover being peeled to expose the compressible applicator's adhesive surface.
Figure 5B:
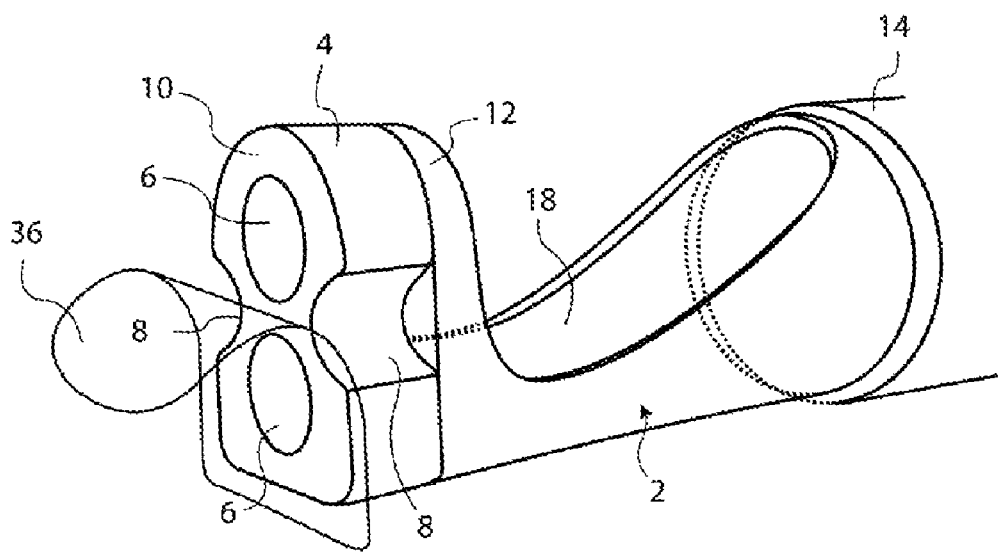

The manner of using the cure through veneer applicator with LED light is first requires an operator to attach a cure through compressible insert 2 to an LED device 22. To accomplish this, the LED devices 22 docking insert docking shaft is placed within compressible cure through inserts 2 docking aperture 16 until the snapping protrusions 20 interlock with the circumferential snapping ring 28 (not shown). Once in place, an attached emulsion cover 36 is peeled away from the compressible applicator 4 to expose the adhesive surface 10 (FIGS. 5A and 5B).

Figure 6:
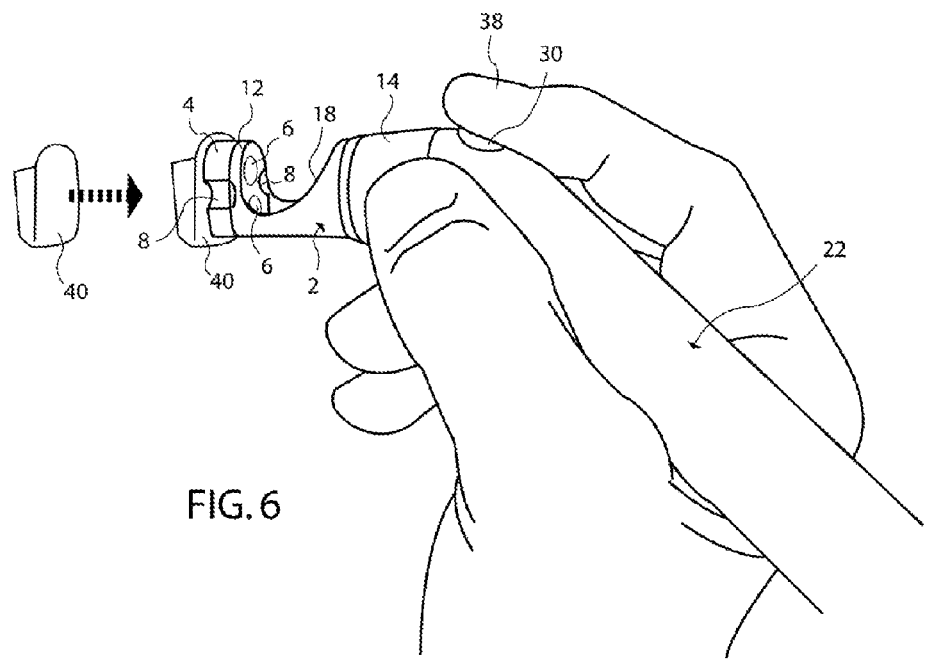
FIG. 6 shows a laminate veneer adhesively placed onto a compressible applicator.
Figure 7:
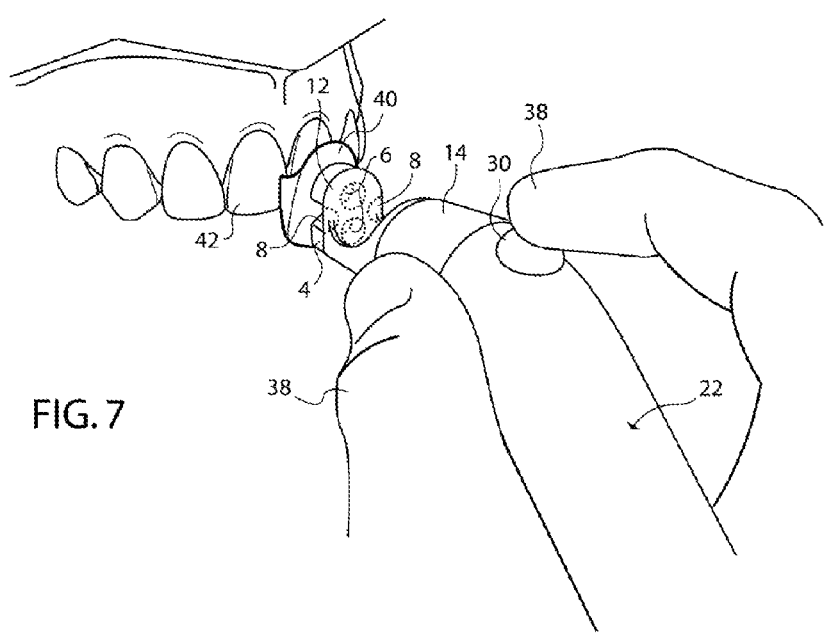
FIG. 7 shows an operator guiding a laminate veneer to a tooth's surface.
Figure 8:
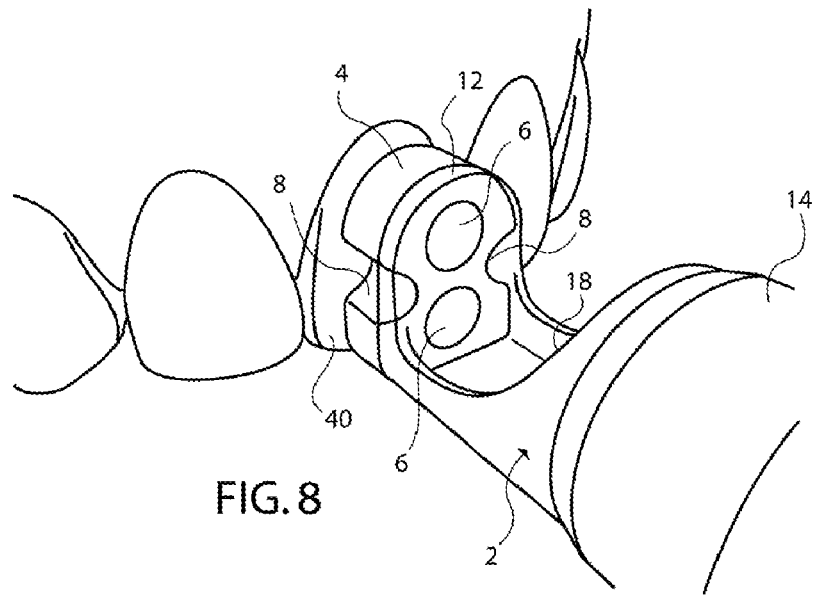
FIG. 8 shows the veneer applied to the tooth's surface
Figure 9:
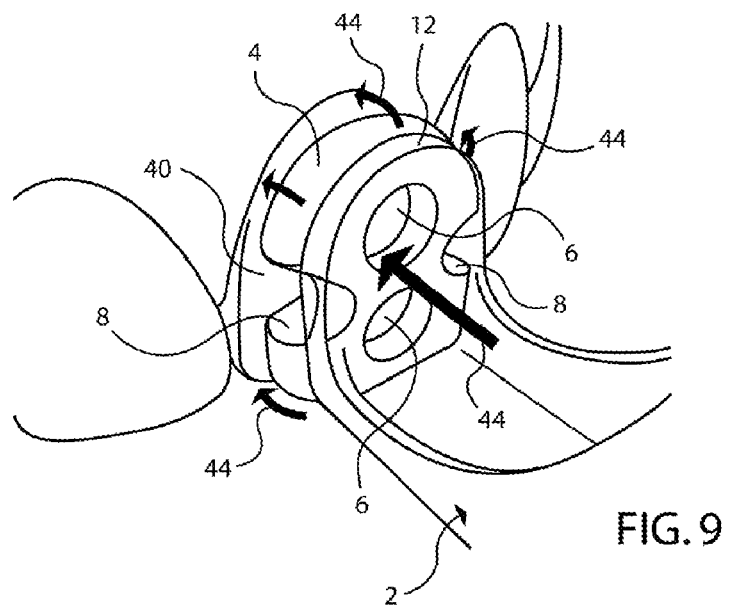
FIG. 9 shows compressive forces adhering the veneer as the operator compressively pushes the applicator against the tooth surface.

Next, the anterior portion of a laminate veneer 40 is placed against the adhesive surface 10 to securely but temporarily hold it for placement (FIG. 6). After the veneer 40 is desirably attached to the adhesive surface 10 the operator 38 guides the bonding surface of the veneer 40 to a tooth surface 42 (FIG. 7). Once proper alignment is achieved, the veneer 40 is placed on the tooth 42. Next, the veneer 40 is placed onto the tooth surface 42 and the compressible applicator 4 is compressed against the veneer 40 (FIG. 8 and FIG. 9). This creates compressive forces 44 which enable to applicator 4 to adaptively adhere the veneer 40 to the tooth surface 42.

Figure 10A:
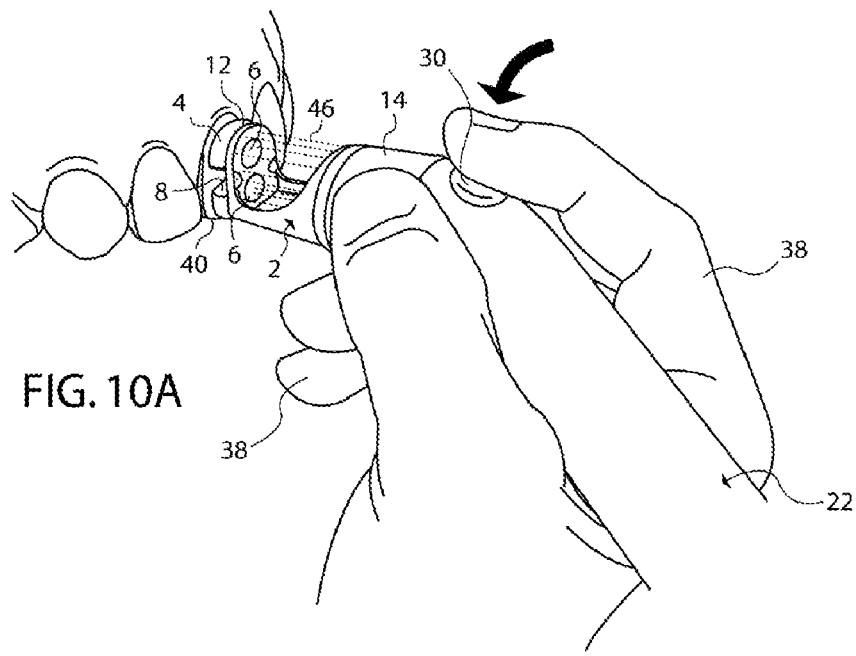
FIGS. 10A to 10B show views of an operator activating the LED power switch to expose the compressive curing apertures with the photo curing light.
Figure 10B:
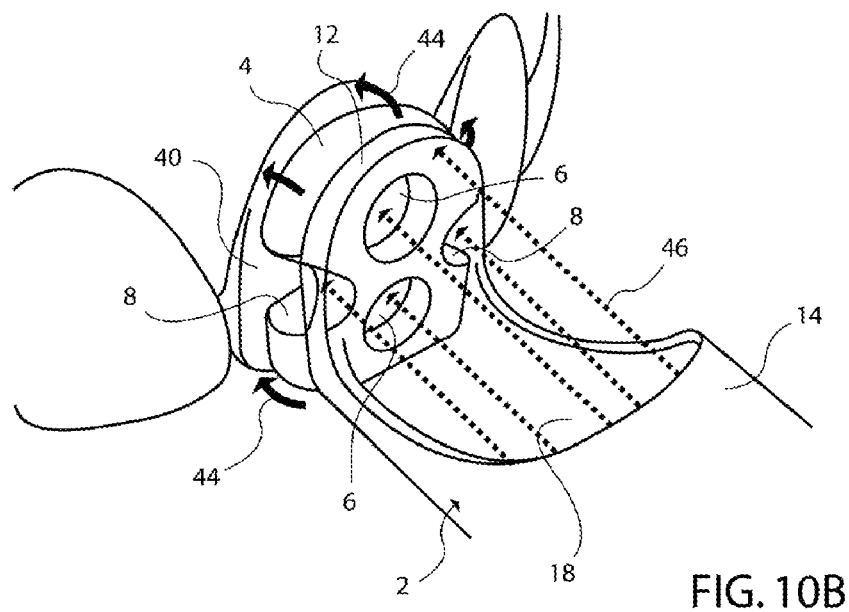

Next, while still maintaining compressive forces 44, an operator 38 depresses the LED power switch 30 to transmit a photo curing light 46 from the LED lamp 26 through the compressible applicator's 4 compressible curing apertures 6 and light channels 8 (FIGS. 10A and 10B) an onto the veneer 40 surface. Finally, with the veneer 40 now bonded to the tooth surface 42, the applicator is removed from the bonded veneer 40 (not shown).

CONCLUSION RAMIFICATIONS AND SCOPE

Accordingly, the reader will see that the cure through veneer applicator with LED can be used to safely place and bond a veneer onto a tooth's surface. Furthermore, the addition of adaptive compressibility will minimize potential veneer fracture. Veneer fracture would result in additional appointments and loss of capital to both operator and associated lab facilities. Lastly, the cure through apertures and attached LED will allow for a one step place and bond process. Furthermore, the veneer applicator with LED has additional advantages in that It permits safe placement of veneers with broad gripping coverage.

Greatly reduces chances of improper bonding that may result from multi-step placement and curing techniques.

Insert design can allow for any possible compressible applicator sizes and configuration.

Insert design ensures that the LED portion will remain contaminate free.

Although the description above contains much specificity, this should not be construed as limiting the scope of the invention but merely as providing illustrations of some of the presently preferred embodiments on this invention. For example, the inserts can have any necessary size, length or structural configuration to optimally attach to the curing light. This includes cylindrical shafts, geometric shafts or a combination of the two. Any number of apertures may be incorporated into any aspect of the insert or compressible applicator. To more securely attach the inserts to LED devices, threading, adhesives or even magnets may be incorporated into insert design.

Furthermore compressible applicators may be made from any material that is suitably compressible. This includes open cell foams, closed cell foams, rubberized materials, or any proprietary amalgamation of suitably compressible materials. Such amalgamations may includes applicators with two or more layers of varying materials or densities of similar materials, multi core applicators (materials within materials), or any suitable material fusion. Compressible applicators may be opaque or transparent or may have any degree of opacity which optimally transmits the desired amount of photo curing light to a surface. Compressible applicators may also have any number of curing apertures. The may be of any size or shape and may be eliminated all together in the event of a transparent photo transmissible material such a clear silicone. Lastly any number of specialized coatings may be incorporated for optimal operation.

Additionally, If the cure through compressible insert is made from fiber optic materials, the insert may assume any configuration which optimally transmits light to a bonding surface. Lastly, the LED device may assume any shape that desirably accommodates cure through inserts and is ergonomically comfortable. Thus, the scope of the invention should be determined by the appended claims and their legal equivalents, rather than by the examples given.

I claim:

1. A laminate veneer applicator with cure light comprising:
    (a)) a hand held photo-curing LED device comprising a docking shaft wherein a LED light source is located within said docking shaft,
    (b) a hollow removably attached photo transmissible, tubular, insert, comprising an insert shaft and a connect portion and terminates in a transparent applicator head which extends transversely in a longitudinal direction from said insert shaft, wherein said connect portion possesses a viewing aperture extending posteriorly from said applicator head to said insert shaft to permit observation of the photo-curing procedure, wherein said docking shaft of said photo-curing device communicates and attaches with said insert shaft,
    (c) an attachable compressible applicator attached to said transparent applicator head to affix a dental veneer, having general dimensions of a tooth's anterior surface and possessing curing apertures to permit transmission of a photo curing light from said LED device.

2. The laminate veneer applicator of claim 1 wherein said docking shaft fits within said insert shaft to permit the transmission of a curing light from said LED device through said insert onto a desired surface.

3. The laminate veneer applicator of claim 1 wherein said docking shaft is cylindrical.

4. The laminate veneer applicator of claim 1 wherein said applicator head is shaped to correlate with a tooth's anterior surface and possesses a transparent flat planar surface to allow for adhesive attachment of said compressible applicator.

5. The laminate veneer applicator of claim 1 wherein said compressible applicator comprising a upper surface having a curved dimension to correlate with a tooth's gingival contour.

6. The laminate veneer applicator of claim 1 wherein said compressible applicator comprising a lower portion that relates to incisal anatomy.

7. The laminate veneer applicator of claim 1 wherein said compressible applicator comprising lateral sides correlating with a tooth's buccal and lingual contours.

8. The laminate veneer applicator of claim 1 wherein said compressible applicator comprising two openings or integrally formed curing apertures within its periphery and two semi circular insets or light channels formed into its periphery to transmit said curing light from said LED device to a bonding surface.

9. The laminate veneer applicator of claim 1 wherein said compressible applicator having adhesive application covered by a removably attached emulsion, the removal of which allows for said operative surface to grip a veneer.

* * * * *